United States Patent [19]

Mulder et al.

[11] 4,010,271

[45] Mar. 1, 1977

[54] NOVEL PYRAZOLINE COMPOUNDS HAVING INSECTICIDAL ACTIVITY

[75] Inventors: Rudolf Mulder; Kobus Wellinga, both of Weesp, Netherlands

[73] Assignee: U.S. Philips Corporation, New York, N.Y.

[22] Filed: May 30, 1975

[21] Appl. No.: 582,308

Related U.S. Application Data

[62] Division of Ser. No. 547,991, Feb. 7, 1975.

[30] Foreign Application Priority Data

Feb. 9, 1972   Netherlands ...................... 7201674

[52] U.S. Cl. .......................... 424/273; 260/294.8 F; 260/294.8 G; 260/294.9; 260/295 E; 260/310 R; 424/263
[51] Int. Cl.² .......................................... A01N 9/22
[58] Field of Search ..................................... 424/273

[56] References Cited

OTHER PUBLICATIONS

Scott et al., *J. Chem. Soc.*, (London), 1971, C, pp. 80–86.

*Primary Examiner*—V. D. Turner
*Attorney, Agent, or Firm*—Frank R. Trifari; Norman N. Spain

[57] ABSTRACT

It has been found that novel pyrazoline compounds have a strong and specific biocidal activity against arthropods and especially insects. In addition to their more direct biocidal activity the novel compounds influence the pattern of motion of arthropods, which results in uncoordinated movements. A highly active substance is, for example, 1-(4-chlorophenylcarbamoyl)-3-(4-chlorophenyl)-5-(4-isopropoxyphenyl)-Δ²-pyrazoline. After the substances have been worked up into preparations they can be used for controlling arthropods and especially insects which are pests in agriculture and horticulture and in industrial products.

32 Claims, No Drawings

NOVEL PYRAZOLINE COMPOUNDS HAVING INSECTICIDAL ACTIVITY

This is a division of copending application Ser. No. 547,991, filed Feb. 7, 1975.

It has been found that novel pyrazoline compounds have a surprising biocidal activity with respect to arthropods, such as mites, but especially insects.

The invention relates to compounds which satisfy the following formula

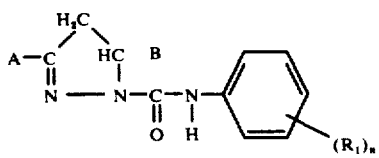

where the symbols have the following meanings:

A is a phenyl group, a phenyl group substituted by 1 or 2 substituents selected from the group comprising a halogen atom, a cyano group, an alkyl group containing from 1 to 4 carbon atoms which may be substituted by halogen, a cycloalkyl group, an alkoxy group containing from 1 to 4 carbon atoms, an alkylthio group containing from 1 to 4 carbon atoms and an amino group substituted by 1 or 2 alkyl groups which contain from 1 to 4 carbon atoms and together with the nitrogen atom of the amino group can form a closed ring which may may contain a second hetero atom selected from a group comprising a sulphur atom, an oxygen atom and a nitrogen atom, or A is a thienyl or pyridyl group which may be substituted by a halogen atom or a lower alkyl group, B is a hydrogen atom, a phenyl group, a phenyl group substituted by from 1 to 3 substituents selected from the group comprising a halogen atom, an alkoxy group containing from 1 to 4 carbon atoms, an alkyl group containing from 1 to 4 carbon atoms which may be substituted by halogen, a cycloalkyl group, a thioalkyl group containing from 1 to 4 carbon atoms, a sulfonylalkyl group containing from 1 to 4 carbon atoms, a dioxyalkylene group containing from 1 to 4 carbon atoms and an amino group substituted by 1 or 2 alkyl groups which each contain from 1 to 4 carbon atoms and together with the nitrogen atom of the amino group can form a closed ring which may contain a second hetero atom, or a furyl, pyrryl, thienyl or pyridyl group which may be substituted by a halogen atom or a lower alkyl group, $R_1$ is a halogen atom, an alkoxy group containing from 1 to 4 carbon atoms, an alkyl group containing from 1 to 4 carbon atoms which may be substituted by halogen, a cylcoalkyl group, a thioalkyl group containing from 1 to 4 carbon atoms, a sulfonylalkyl group containing from 1 to 4 carbon atoms, a cyano group, a nitro group or an amino group substituted by 1 or 2 alkyl groups which together with the nitrogen atom of the amino group can form a ring which may contain a second hereto atom, and $n$ is 1 or 2.

It should be noted that when A represents a phenyl group which contains two substituents the latter are not allowed to occupy the 2,6 positions of the phenyl group. Also $(R_1)_n$ must not be a 2,6 substituent.

The biocidal activity of the novel compounds according to the invention has been found in a biological evaluation investigation in which test solutions and test suspensions of the active substances have been tested for their biocidal activity with respect to, inter alia *Leptinotarsa decemlineata, Pieris brassicae, Aedes aegypti, Delia brassicae, Musca domestica, periplaneta americana, Phyllocoptruta oleivora,* Heteroptera sp. and Aphididae sp.

The active substances have been tested in different concentrations in a range from 1,000 mg of active substance per liter of test liquid to 1 mg of active substance per liter of test liquid. Thus, for example, in the test for activity relative to beetles, larvae of beetles, caterpillars, maggots and mosquito larvae, the starting concentration was 100 mg of active substance per liter, after which in proportion to the activity found the concentration was successively reduced to 30, 10, 3 and 1 mg of active substance per liter of test liquid.

The results of the evaluation investigation show that the substances according to the invention have a good biocidal activity with respect to arthropods and specially with respect to insects. In this connection it should be pointed out that the aforementioned *Arthropoda* sp. are not limitative. The substances according to the invention are active also, for example, against weevils (*Sitophilus granarius*) and against insects which attack industrial products, such as the carpet beetle (*Attagenus piceus*) and the webbing cloths moth (*Tineola bisselliella*).

More particularly it has been found that especially beetles, larvae of beetles, caterpillars, maggots and mosquito larvae are highly sensitive to the substances according to the invention. For example, the larvae of the colorado beetle (*Leptinotarsa decemlineata*) is efficiently controlled even at concentrations of from 3 to 30 p.p.m. of active substance.

Surprisingly it has been found that the substances according to the invention have a very specific action mechanism. In addition to a more direct biocidal activity based on the toxicity of the substances for arthropods, an influence on the motion pattern of the treated arthropods has been observed. The change in the motion pattern consists mainly in the occurrence of uncoordinated movements which on the one hand cause immobility of the treated insect and also produce a strong increase in the intensity of the movements. The result of the disturbed motion pattern is that the insect cannot maintain its position on plant leaves, but drops off and hence can no longer ingest food. A further cause of its death is dehydration.

The biological evaluation investigation further has shown that especially the compounds which satisfy the following formulae have a strong biocidal activity:

I Compounds of the formula:

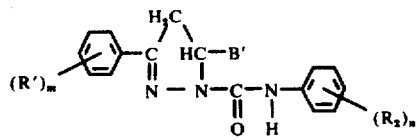

where
R' is a hydrogen atom, a halogen atom, a cyano group, an alkoxy group containing from 1 to 4 carbon atoms or an alkyl group containing from 1 to 4 carbon atoms, B' is a hydrogen atom, a phenyl group or a phenyl group substituted by from 1 to 3 substituents selected from the group comprising a halogen atom, an alkoxy group containing from 1 to 4 carbon atoms and an alkyl group containing from 1 to 4 carbon atoms, $R_2$ is a halogen atom or an alkyl group, containing from 1 to 4 carbon atoms, $m$ is 1 or 2 and $n$ is 1 or 2, on the understanding that $(R')_m$ and $(R_2)_n$ are not 2,6 disubstitutions.

II Compounds of the formula

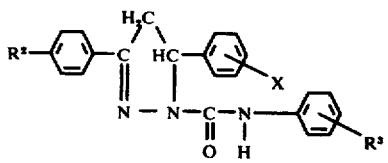

where
- $R^2$ is a hydrogen atom, a halogen atom, a cyano group, an alkyl, alkoxy or thionyl group containing from 1 to 4 carbon atoms, a cycloalkyl group or an amino group substituted by 1 or 2 alkyl groups, where the alkyl groups contain from 1 to 4 carbon atoms and together with the nitrogen atom of the amino group may a closed ring which may contain a second hetero atom,
- $R^3$ is a substituent in the para position selected from the group comprising a halogen atom, an alkyl group which contains from 1 to 4 carbon atoms and may be substituted with halogen, a cycloalkyl group, a thioalkyl group containing from 1 to 4 carbon atoms, a sulfonylalkyl group containing from 1 to 4 carbon atoms, a cyano group and an amino group substituted by 1 or 2 alkyl groups which contain from 1 to 4 carbon atoms and further together with the nitrogen atom of the amino group can form a closed ring which may contain a second hetero atoms, or
- $R^3$ is a 3,4-dichloro substituent, and
- X is a substituent in the para position which is selected from the group comprising a hydrogen atom, a halogen atom, an alkyl group containing from 1 to 4 carbon atoms, a cycloalkyl group, an alkoxy group, containing from 1 to 4 carbon atoms and an amino group substituted by 1 or 2 alkyl groups which contain from 1 to 4 carbon atoms and together with the nitrogen atom of the amino group can form a closed ring which may contain a second hetero atom, or
- $R^4$ is a 2,4 or 3,4 disubstituent, the substituents being selected from the group comprising a halogen atom, a lower alkyl group and a dioxyalkylene group, or
- $R^4$ is a 2,4,6-trihalogen group.

III Compounds of the formula

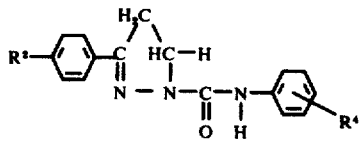

where
- $R^2$ has the aforementioned meaning and
- $R^4$ is a 3,4-dichloro group or a substituent in the para position selected from the group comprising a halogen atom, an alkyl group which contains from 1 to 4 carbon atoms and may be substituted by halogen, a cycloalkyl group, a thioalkyl group containing from 1 to 4 carbon atoms, a sulfonylalkyl group containing from 1 to 4 carbon atoms, a cyano group, a nitro group and an amino group substituted by 1 or 2 alkyl groups which contain from 1 to 4 carbon atoms and together with the nitrogen atom of the amino group can form a closed ring which may contain a second hetero atom, IV Compounds of the formula

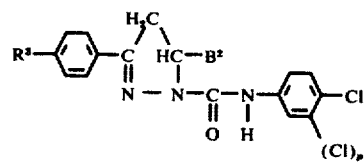

where
- $R^3$ is a hydrogen atom, a halogen atom, a cyano group or a methoxy group,
- $B^2$ represents a hydrogen atom, a phenyl group, a 4-chlorophenyl group, a 4-methoxy phenyl group or a 2,4-dichlorophenyl group, and
- $p$ is 0 or 1.

Examples of highly active substances according to the invention which even in a concentration of from 3 to 10 p.p.m. cause complete mortality of Leptinotarsa decemlineata or Pieris brassicae are listed below. The name of each substance is followed by its melting point.

1. 1-(4-chlorophenylcarbamoyl)-3-(4-chlorophenyl)-5-(chlorophenyl)-Δ²-pyrazoline. Melting point 224° C.
2. 1-(4-sulfonylmethylphenylcarbamoyl)-3-(4-chlorophenyl)-5-(4-chlorophenyl)-Δ²-pyrazoline. Melting point 170° C.
3. 1-(4-sulfonylphenylcarbamoyl)-3-(4-chlorophenyl)-5-(4-chlorophenyl-Δ²-pyrazoline. Melting point 150° C.
4. 1-(4-chlorophenylcarbamoyl)-3-(4-chlorophenyl)-5-(4-isopropoxyphenyl)-Δ²-pyrazoline. Melting point 166° C.
5. 1-(4-t.butylphenylcarbamoyl)-3-(4-chlorophenyl)-5-(4-chlorophenyl)-Δ²-pyrazoline. Melting point 199° C.
6. 1-(4-n.propylphenylcarbamoyl)-3-(4-chlorophenyl)-5-(4-chlorophenyl)-Δ²-pyrazoline. Melting point 149° C.
7. 1-(4-ethylphenylcarbamoyl)-3-(4-chlorophenyl)-5-(4-chlorophenyl)-Δ²-pyrazoline. Melting point 181° C.
8. 1-(trifluoromethylphenylcarbamoyl)-3-(4-chlorophenyl)-5-(4-chlorophenyl)-Δ²-pyrazoline. Melting point 206° C.
9. 1-(4-chlorophenylcarbamoyl)-3-(4-chlorophenyl)-5-(fluorophenyl)-Δ²-pyrazoline. Melting point 176° C.
10. 1-(4-chlorophenylcarbamoyl)-3-(4-chlorophenyl)-5-(4-ethylphenyl)-Δ²-pyrazoline. Melting point 235° C.

11. 1-(4-chlorophenylcarbamoyl)-3-(4-chlorophenyl)-5-(4-t.butylphenyl)-Δ²-pyrazoline. Melting point 222° C.
12. 1-(4-chlorophenylcarbamoyl)-3-(4-chlorophenyl)-5-(2-methyl-4-chlorophenyl)-Δ²-pyrazoline. Melting point 184° C.
13. 1-(4-chlorophenylcarbamoyl)-3-(4-dimethylaminophenyl)-5-(4-chlorophenyl)-Δ²-pyrazoline. Melting point 236° C.
14. 1-(4-chlorophenylcarbamoyl)-3-(4-chlorophenyl)-5-(2,4-dichlorophenyl)-Δ²-pyrazoline. Melting point 166° C.
15. 1-(4-chlorophenylcarbamoyl)-3-phenyl-5-(4-methoxyphenyl)-Δ²-pyrazoline. Melting point 164° C.
16. 1-(4-chlorophenylcarbamoyl)-3-(4-bromophenyl)-5-phenyl-Δ²-pyrazoline. Melting point 158° C.
17. 1-(4-chlorophenylcarbamoyl)-3-(phenyl)-5-(2,4-dichlorophenyl)-Δ²-pyrazoline. Melting point 184° C.
18. 1-(4-chlorophenylcarbamoyl)-3-phenyl-5-(4-chlorophenyl)-Δ²-pyrazoline. Melting point 160° C.
19. 1-(3,4-dichlorophenylcarbamoyl)-3-phenyl-5-(1-methoxyphenyl)-Δ²-pyrazoline. Melting point 170° C.
20. 1-(4-chlorophenylcarbamoyl)-3-(4-chlorophenyl)-5-phenyl-Δ²-pyrazoline. Melting point 174° C.
21. 1-(4-chlorophenylcarbamoyl)-3-(4-cyanophenyl)-5-phenyl-Δ²-pyrazoline. Melting point 210° C.
22. 1-(3,4-dichlorophenylcarbamoyl)-3-(4-cyanophenyl)-5-phenyl-Δ²-pyrazoline. Melting point 140° C.
23. 1-(4-chlorophenylcarbamoyl)3-(4-chlorophenyl)-5(4-methoxyphenyl)-Δ²-pyrazoline. Melting point 197° C.
24. 1-(4-chlorophenylcarbonyl)-3-(4-chlorophenyl)-5-(4-i.propylphenyl)-Δ²-pyrazoline. Melting point 190° C.
25. 1-(4-chlorophenylcarbamoyl)-3-(4-chlorophenyl)-5(4-n-propylphenyl)-Δ²-pyrazoline. Melting point 178° C.
26. 1-(4-sulfonylphenylcarbamoyl)-3-(4-chlorophenyl)-5(4-t.butylphenyl)-Δ²-pyrazoline. Melting point 191° C.
27. 1-(iodophenylcarbamoyl)-3-(chlorophenyl)-5-(4-chlorophenyl)-Δ²-pyrazoline. Melting point 228° C.
28. 1-(4-chlorophenylcarbonoyl)-3-(4-iodophenyl)-5-(4-chlorophenyl)-Δ²-pyrazoline. Melting point 206° C.
29. 1-(4-chlorophenylcarbamoyl)-3-(4-chlorophenyl)-5-(5-chlorothienyl-2)-Δ²-pyrazoline. Melting point 166° C.
30. 1-(4-chlorophenylcarbamoyl)-3-(4-chlorophenyl)-5(furyl-2)-Δ²-pyrazoline. Melting point 207° C.
31. 1-(4-chlorophenylcarbamoyl)-3-(4-chlorophenyl)-5-(3-methylfuryl-2)-Δ²-pyrazoline. Melting point 190° C.
32. 1-(4-chlorophenylcarbamoyl)-3-(4-chlorophenyl)-5-(5-methylthienyl-2)-Δ²-pyrazoline. Melting point 154° C.
33. 1-(4-chlorophenylcarbamoyl)-3-(pyridyl-2)-5-(4-chlorophenyl)-Δ²-pyrazoline. Melting point 205° C.
34. 1-(4-chlorophenylcarbamoyl)-3-(4-chlorophenyl)-5-(5-chlorofuryl-2)-66 ²-pyrazoline. Melting point 195° C.
35. 1-(4-chlorophenylcarbamoyl)-3-(4-chlorophenyl)-5-(3,4-dioxymethylenephenyl)-Δ²-pyrazoline. Melting point 193° C.
36. 1-(4-chlorophenylcarbamoyl)-3-(4-chlorophenyl)-5-(4-dimethylaminophenyl)-Δ²-pyrazoline. Melting point 189° C.
37. 1-(4-chlorophenylcarbamoyl)-3-phenyl-Δ²-pyrazoline. Melting point 148° C.
38. 1-(4-chlorophenylcarbamoyl)-3-(4-chlorophenyl)-Δ²-pyrazoline. Melting point 175° C.
39. 1-(4-chlorophenylcarbamoyl)-3-(4-fluorophenyl)-Δ²-pyrazoline. Melting point 150° C.
40. 1-(4-chlorophenylcarbamoyl)-3-(4-bromophenyl)-Δ²-pyrazoline. Melting point 144° C.
41. 1-(4-iodophenylcarbamoyl)-3-(4-chlorophenyl)-Δ²-pyrazoline. Melting point 162° C.
42. 1-(4-n.propylphenylcarbamoyl)-3-(4-chlorophenyl)-Δ²-pyrazoline. Melting point 151° C.
43. 1-(3,4-dichlorophenylcarbamoyl)-3-phenyl-Δ²-pyrazoline. Melting point 168° C.
44. 1-(3,4-dichlorophenylcarbamoyl)-3-(4-chlorophenyl)-Δ²-pyrazoline. Melting point 187° C.
45. 1-(3,4-dichlorophenylcarbamoyl)-3-(4-bromophenyl)-Δ²-pyrazoline. Melting point 192° C.
46. 1-(4-bromophenylcarbamoyl)-3-(4-chlorophenyl)-Δ²-pyrazoline. Melting point 181° C.
47. 1-(4-chlorophenylcarbamoyl)-3-(4-isopropoxyphenyl)-Δ²-pyrazoline. Melting point 141° C.
48. 1-(4-ethoxyphenylcarbamoyl)-3-(4-chlorophenyl)Δ²-pyrazoline. Melting point 140° C.
49. 1-(4-ethylsulfonylphenylcarbamoyl)-3(4-chlorophenyl)-Δ²-pyrazoline. Melting point 187° C.
50. 1-(4-chlorophenylcarbamoyl)-3-(4-ethylphenyl)-Δ²-pyrazoline. Melting point 116° C.
51. 1-(4-chlorophenylcarbamoyl)-3-(4-isopropylphenyl)-Δ²-pyrazoline. Melting point 131° C.
52. 1-(4-chlorophenylcarbamoyl)-3-(4-iodophenyl)-Δ²-pyrazoline. Melting point 165° C.
53. 1-(4-cyanophenylcarbamoyl)-3-(4-chlorophenyl)-Δ²-pyrazoline. Melting point 210° C.
54. 1-(4-nitrophenylcarbamoyl)-3-(4-chlorophenyl)-Δ²-pyrazoline. Melting point 225° C.
55. 1-(4-chlorophenylcarbamoyl)-3-(4-dimethylaminophenyl)Δ²-pyrazoline. Melting point 189° C.

Examples of substances according to the invention which are slightly less active than the preceding compounds are:
56. 1-(3,4-dichlorophenylcarbamoyl)-3-(phenyl-5-(4-chlorophenyl)-Δ²-pyrazoline. Melting point 182° C.
57. 1-(3,4-dichlorophenylcarbamoyl)-3-(4-chlorophenyl)-5-phenyl-Δ²-pyrazoline. Melting point 188° C.
58. 1-(3,4-dichlorophenylcarbamoyl)-3-phenyl-5-(2,4-dichlorophenyl)-Δ²-pyrazoline. Melting point 189° C.
59. 1-(3,4-dichlorophenyl)-3-(4-chlorophenyl)-5-(4-chlorophenyl)-Δ²-pyrazoline. Melting point 208° C.

60. 1-(4-chlorophenylcarbamoyl)-3-(4-methoxyphenyl)-5-phenyl-Δ²-pyrazoline. Melting point 157° C.
61. 1-(3,4-dichlorophenylcarbamoyl)-3-(4-bromophenyl)-5-phenyl-Δ²-pyrazoline. Melting point 188° C.
62. 1-(4-chlorophenylcarbamoyl)-3-(3-methoxyphenyl)-5-phenyl-Δ²-pyrazoline. Melting point 145° C.
63. 1-(4-chlorophenylcarbamoyl)-3-(3-chlorophenyl)-5-phenyl-Δ²-pyrazoline. Melting point 196° C.
64. 1-(3,4-dichlorophenylcarbamoyl)-3-(3-chlorophenyl)-5-phenyl-Δ²-pyrazoline. Melting point 195° C.
65. 1-(4-chlorophenylcarbamoyl)-3-(4-chlorophenyl)-5-(4-n.butylphenyl)-Δ²Melting point 154° C.
66. 1-(4-fluorophenylcarbamoyl)-3-(4-chlorophenyl)-5-(4-n.butylphenyl)-Δ²-pyrazoline. Melting point 190° C.
67. 1-(4-methylphenylcarbamoyl)-3-(4-chlorophenyl)-5-(4-n.butylphenyl)-Δ²-pyrazoline. Melting point 220° C.
68. 1-(4-chlorophenylcarbamoyl)-3-(4-chlorophenyl)-5-(3-chlorophenyl)-Δ²-pyrazoline. Melting point 207° C.
69. 1-(4-chlorophenylcarbamoyl)-3-(4-thiomethylphenyl-5-(4-chlorophenyl)-Δ²-pyrazoline. Melting point 188° C.
70. 1-(4.butylphenylcarbamoyl)-3-(4-chlorophenyl)-5-(4-chlorophenyl)-Δ²-pyrazoline. Melting point 138° C.
71. 1-(4-chlorophenylcarbamoyl)-3-(4-chlorophenyl)-5-(2,4,6-trichlorophenyl)-Δ²-pyrazoline. Melting point 191° C.
72. 1-(4-chlorophenylcarbamoyl)-3-(4-t.butylphenyl)-5-(4-chlorophenyl)-Δ²-pyrazoline. Melting point 203° C.
73. 1-(4-thiomethylphenylcarbamoyl)-3-(4-chlorophenyl)-5-(4-chlorophenyl)-Δ²-pyrazoline. Melting point 191° C.
74. 1-(4-chlorophenylcarbamoyl)-3-(4-i.propoxyphenyl)-5-(4-chlorophenyl)-Δ²-pyrazoline. Melting point 116° C.
75. 1-(4-chlorophenylcarbamoyl)-3-(4-n.butylphenyl)-5-(4-chlorophenyl)-Δ²-pyrazoline. Melting point 78° C.
76. 1(4-chlorophenylcarbamoyl)-3-(bromophenyl)-5-(4-chlorophenyl)-Δ²-pyrazoline. Melting point 219° C.
77. 1-(4-n.butylphenylcarbamoyl)-3-(4-chlorophenyl)-5-(4-n.butylphenyl)-Δ²-pyrazoline. Melting point 135° C.
78. 1-(4-chlorophenylcarbamoyl)-3-(4-ethylphenyl)-5-(4-chlorophenyl)-Δ²-pyrazoline. Melting point 206° C.
79. 1-(4-chlorophenylcarbamoyl)-3-(4-cyclohexylphenyl)-5-(4-chlorophenyl)-Δ²-pyrazoline. Melting point 175° C.
80. 1-(4-chlorophenylcarbamoyl)-3-(4-t.butylphenyl)-5-(4-chlorophenyl)-Δ²-pyrazoline. Melting point 204° C.
81. 1-(2-chlorophenylcarbamoyl)-3-(4-chlorophenyl)-5-(4-chlorophenyl)-Δ²-pyrazoline. Melting point 225° C.
82. 1-(3-chlorophenylcarbamoyl)-3-(4-chlorophenyl)-5-(4-chlorophenyl)-Δ²-pyrazoline. Melting point 192° C.
83. 1-(2,4-dichlorophenylcarbamoyl)-3-(4-chlorophenyl)-5-(4-chlorophenyl)-Δ²-pyrazoline. Melting point 192° C.
84. 1-(4-dimethylaminophenylcarbamoyl)-3-(4-chlorophenyl)-5-(4-chlorophenyl)-Δ²-pyrazoline. Melting point 178° C.
85. 1-(4-chlorophenylcarbamoyl)-3-(4-morpholinophenyl)-5-(4-chlorophenyl)-Δ²-pyrazoline. Melting point 160° C.
86. 1-(4-chlorophenylcarbamoyl)-3-(4-piperidinophenyl)-5-(4-chlorophenyl)-Δ²-pyrazoline. Melting point 163° C.
87. 1-(4-chlorophenylcarbamoyl)-3-(4-pyrazolidinophenyl)-5-(4-chlorophenyl)-Δ²-pyrazoline. Melting point 208° C.
88. 1-(4-chlorophenylcarbamoyl)-3-(5-chlorothienyl-2)-5-(4-chlorophenyl)-Δ²-pyrazoline. Melting point 196° C.
89. 1-(4-chlorophenylcarbamoyl)-3-(4-chlorophenyl)-5-(pyrryl-2)-Δ²-pyrazoline. Melting point 230° C.
90. 1-(4-chlorophenylcarbamoyl)-3-(4-chlorophenyl)-5-(pyridyl-3)-Δ²-pyrazoline. Melting point 205° C.
91. 1-(4-chlorophenylcarbamoyl)-3-(pyridyl-3)-5-(4-chlorophenyl)-Δ²-pyrazoline. Melting point 105° C.
92. 1-(4-chlorophenylcarbamoyl)-3-(4-chlorophenyl)-5-(pyridyl-2)-Δ²-pyrazoline. Melting point 243° C.
93. 1-(4-chlorophenylcarbamoyl)-3-(4-chlorophenyl)-5-(pyridil-4)-Δ²-pyrazoline. Melting point 239+ C.
94. 1-(4-chlorophenylcarbamoyl)-3-(3,4-dimethyloxyphenyl)-5-(4-chlorophenyl)-Δ²-pyrazoline. Melting point 163° C.
95. 1-(4-chlorophenylcarbamoyl)-3-(4-chlorophenyl)-5-(1-methylpyrryl-2)-Δ²-pyrazoline. Melting point 207°
96. 1-(3,4-dichlorophenylcarbamoyl)-3-(4-methoxyphenyl)-Δ²-pyrazoline. Melting point 170° C.
97. 1-(4-chlorophenylcarbamoyl)-3-(4-methoxyphenyl)-Δ²-pyrazoline. Melting poing 132° C.
98. 1-(3,4-dichlorophenylcarbamoyl)-3-(4-fluorophenyl)-Δ²-pyrazoline. Melting point 162° C.
99. 1-(4-chlorophenylcarbamoyl)-3-(3-methoxyphenyl)-Δ²-pyrazoline. Melting point 129° C.
100. 1-(3,4-dichlorophenylcarbamoyl)-3-(3-methoxyphenyl)-Δ²-pyrazoline. Melting point 136° C.
101 1-(3,4-dichlorophenylcarbamoyl)-3-(3-chlorophenyl)-Δ²-pyrazoline. Melting point 180° C.
102. 1-(4-chlorophenylcarbamoyl)-3-(3-chlorophenyl)-Δ²-pyrazoline. Melting point 161° C.
103. 1-(4-chlorophenylcarbamoyl)-3-(4-methoxyphenyl)-Δ²-pyrazoline. Melting point 139° C.
104. 1-(4-methylphenylcarbamoyl)-3-(4-methylphenyl)-Δ²-pyrazoline. Melting point 159° C.
105. 1-(4-ethylphenylcarbamoyl)-3-(4-n.butylphenyl)-Δ²-pyrazoline. Melting point 147° C.
106. 1-(4-methylphenycarbamoly)-3-(4-chlorophenyl)-Δ²-pyrazoline. Melting point 181° C.
107. 1-(4-sulfonylmethylphenylcarbamoyl)-3(4-chlorophenyl)-Δ²-pyrazoline. Melting point 225° C.

108. 1-(4-chlorophenylcarbamoyl)-3-(4.propylphenyl)-Δ²-pyrazoline. Melting point 153° C.
109. 1-(4-n.butylphenylcarbamoyl)-3-(4-chlorophenyl)-Δ²-pyrazoline. Melting point 134° C.
110. 1-(4-sulfonylethylphenylcarbamoyl)-3-(4-ethylphenyl)-Δ²-pyrazoline. Melting point 172° C.
111. 1-(4-chlorophenylcarbamoyl)-3-(4-thiomethylphenyl)-Δ²-pyrazoline. Melting point 154° C.
112. 1-(4-chlorophenylcarbamoyl)-3-(4-t.butylphenyl)-Δ²-pyrazoline. Melting point 150° C.
113. 1-phenylcarbamoyl-3-phenyl-Δ²-pyrazoline. Melting point 160° C.
114. 1-(4-fluorophenylcarbamoyl)-3-(4-chlorophenyl)-Δ²-pyrazoline. Melting point 173° C.
115. 1-(4-fluorophenylcarbamoyl)-3-phenyl-Δ²-pyrazoline. Melting point 137° C.
116. 1-(4-t.butylphenylcarbamoyl)-3-phenyl-Δ²-pyrazoline. Melting point 146° C.
117. 1-(4-n.propylphenylcarbamoyl)-3-phenyl-Δ²-pyrazoline. Melting point 120° C.

The first 15 compounds of the above list of 117 substances have an activity such that even at a dosage of 3 p.p.m. complete or substantially complete mortality of larvae of the colorado beetle and/or cabbage worm is obtained. An equally high level of activity is found for the compounds listed as numbers 37 to 42. It has further been found that the substances which have a hydrogen atom at the position 5 of the pyrazoline ring, such as the substances listed as numbers 37 to 55, although they may not show a very high activity in hothouse tests, show unexpectedly good results in the field. Interesting compounds from this group are the aforementioned substances of the numbers 37 to 42 and the compounds 47 to 51.

Owing to their insecticide activity the substances according to the invention may be used for controlling insects and plant parasitic mites in agriculture and horticulture, such as caterpillars, mosquito larvae, cockroaches, cicadas, larvae of beetles, in particular of the Colorado beetles, citrus rust mite and for controlling weevils, such as Sitophilus granarius, and insects which attack industrial products such, for example, as wood and textile materials. Examples of insects which attack industrial products are the moth, the carpet beetle, the capricorn beetle and the woodborer.

For practical use the compounds according to the invention are worked up into preparations. In these preparations the active substance is mixed with a solid carrier material or dissolved or dispersed in a liquid carrier material, as the case may be in conjunction with adjuvants, such as surfactants and stabilizers.

Examples of preparations according to the invention are aqueous solutions and dispersions, oil solutions and oil dispersions, pastes, dusts, wettable powders, miscible oils, granules, invert emulsions, aerosol preparations and fumigating candles.

Wettable powders, pastes and miscible oils are concentrated preparations which are diluted with water before or during use.

The invert emulsions are mainly used for air application, where large areas are treated with a comparatively small amount of preparation. The invert emulsion may be prepared in the spraying apparatus shortly before, or even during, the spraying operation by emulsifying water in an oil solution or an oil dispersion of the active substance. Hereinafter some examples of preparations are described more fully.

Granular preparations are produced, for example, by taking up the active substance in a solvent and by using the resulting solution, as the case may be in the presence of a binder, to impregnate a granular carrier material, such as porous granules (for example pumice and attaclay). mineral non-porous granules (sand or ground marl) or organic granules (for example dried coffee grounds and chopped tobacco stems).

A granular preparation may alternatively be produced by compressing the active substance together with powdered minerals in the presence of lubricants and binders and by disintegrating and straining the comprimate to the desired grain size.

Dusts are obtainable by intimately mixing the active substance with an inert solid carrier material in a concentration of from 1 to 50% by weight. Examples of suitable solid carrier materials are talc, caolin, pipe clay, diatom earth, dolomite, gypsum, chalk, bentonite, attapulgite and colloidal $SiO_2$ or mixtures of these and simular substances. Alternatively organic carrier materials such, for example, as ground walnut shells may be used.

Wettable powders are produced by mixing from 10 to 80 parts by weight of a solid inert carrier such, for example, as the aforementioned carrier materials with from 10 to 80 parts by weight of the active substance, from 1 to 5 parts by weight of a dispersing agent such, for example, as the ligninsulfonates or alkylnaphthalene sulfonates known for this purpose and preferably also from 0.5 to 5 parts by weight of a wetting agent, such as fatty alcohol sulfates, alkylarylsulfonates or fatty acid condensation products.

To produce miscible oils the active compound is dissolved or finely divided in a suitable solvent which preferably is poorly miscible with water, an emulsifier being added to the resulting solution. Examples of suitable solvents are xylene, toluene, high-aromatic petroleum distillates, for example solvent naphtha, distilled tar oil and mixtures of these liquids. Examples of suitable emulsifiers are alkylphenoxypolyglycol ethers, polyoxyethylene sorbitan esters of fatty acids or polyoxyethylene sorbitol esters of fatty acids. The concentration of the active compound in these miscible oils is not restricted within narrow limits and may vary between 2% and 50% by weight. A suitable liquid highly concentrated primary composition other than a miscible oil is a solution of the active substance in a liquid which is readily miscible with water, for example, acetone, to which solution a dispergent and, as the case may be, a wetting agent are added. When such a primary composition is diluted with water shortly before or during the spraying operation an aqueous dispersion of the active substance is obtained.

An aerosol preparation according to the invention is obtained in the usual manner by incorporating the active substance or a solution thereof in a suitable solvent in a volatile liquid suitable for use as a propellant such, for example, as a mixture of chlorine and fluorine derivatives of methane and ethane.

Fumigating candles or fumigating powders, i.e. preparations which when burning are capable of emitting a pesticidal smoke, are obtained by taking up the active substance in a combustible mixture which may, for example, comprise a sugar or a wood, preferably in the ground form, as a fuel, a substance to sustain combustion such, for example, as ammonium nitrate or potassium chlorate, and furthermore a substance for retarding combustion, for example kaolin, bentonite and/or colloidal silicic acid.

In addition to the aforementioned ingredients the preparations according to the invention may also contain other substances commonly used in preparations of this kind.

For example, a lubricant, such as calcium stearate or magnesium stearate, may be added to a wettable powder or to a mixture to be granulated. Furthermore there may, for example, be added "adhesives" such as polyvinylalcoholcellulose derivatives or other colloidal materials, such as casein, to improve the adherence of the pesticide to the surface to be protected.

The preparations according to the invention may also contain known pesticidal compounds. This expands the spectrum of activity of the preparation and may give rise to synergism.

The following known insecticidal, fungicidal and acaricidal compounds are suitable for use in such a combined preparation.

Insecticides such as:
1. Chlorinated hydrocarbons, for example 2,2-bis(p-chlorophenyl)-1,1,1-trichloroethane and hexachloroepoxyoctahydrodimethanonaphthalene;
2. Carbamates, for example N-methyl-1-naphthyl carbamate;
3. Dinitrophenols, for example 2-methyl-4,6-dinitrophenol and 2-(2-butyl)-4,6-dinitrophenyl-3,3-dimethylacrylate;
4. Organic phosphorus compounds, such as dimethyl-2-methoxy-carbonyl-1-methylvinyl phosphate; 0,0-diethyl-0-p.nitrophenylphosphorus thioate; N-monomethylamide of 0,0-dimethyldithiophosphorylacetic acid;

Acaricides such as:
5. Diphenylsulfides, for example p-chlorobenzyl or p-chlorophenyl sulfide and 2,4,4'-5-tetrachloridiphenylsulfide;
6. Diphenylsulfonates, for example p-chlorophenylbenzenesulfonate;
7. Methylcabinols, for example 4,4-dichloro-a-trichloromethylbenzhydrol;
8. Quinoxaline compounds, such as methylquinoxaline dithiocarbonate;

Fungicides such as:
9. Organic mercury compounds, for example phenylmercuryacetate and methylmercurycyanoguanide;
10. Organic tin compounds, for example triphenyltinhydroxide and triphenyltinacetate;
11. Alkylenebisdithiocarbamates, for example, zincethylenebisthiocarbamate and manganoethylenebisthiocarbamate; and furthermore
12. 2,4-dinitro-6-(2-octyl-phenylcrotonate),
    1-bis(dimethylamino)phosphoryl-3-phenyl-5-amino-1,2,4-triazole,
    6-methylquinoxaline-2,3-dithiocarbonate,
    1,4-dithioantraquinone-2,3-dicarbonitrile,
    N-trichloromethylthiophthalimide,
    N-trichloromethylthiotetrahydrophthalimide,
    N-(1,1,2,2-tetrachloroethylthio)-tetrahydrophthalimide,
    N-dichlorofluoromethylthio-N-phenyl-N'-dimethylsulfonyldiamide
and tetrachloroisophthalonitrile.

The dosage of the preparation according to the invention which is desirable for practical use will obviously depend upon various factors, such as field of use, active substance chosen, form of preparation and nature and intensity of the infection.

For use in agriculture in general a dose corresponding to from 0.5 to 5 kg of active substance per hectare will provide good results.

The compounds according to the invention are novel substances which may be prepared by methods known for the preparation of similar substances or by analogous methods. For example, the compounds according to the invention may be prepared by reacting a compound of the formula

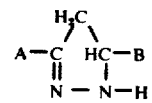

where A and B have the aforementioned meanings, with a compound of the formula

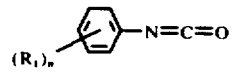

where $R_1$ and $n$ have the aforementioned meanings, a compound of the formula

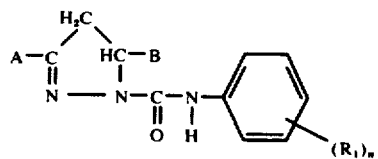

being formed.

The reaction proceeds in the presence of a solvent, such an an other, for example diethylether. If desired, a catalyst, such as an organic base, for example triethylamine, may be added.

The starting materials for the aforementioned process may be obtained in two manners. They may be prepared by using the following reactions:

I

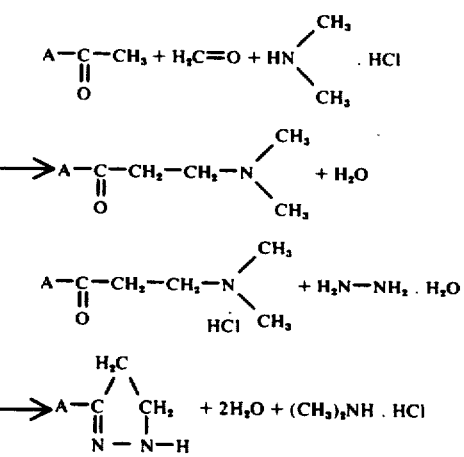

The second method of producing the starting materials comprises the following reactions:

II a 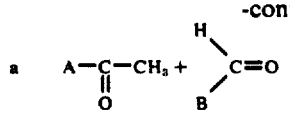

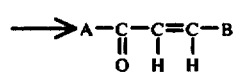

b 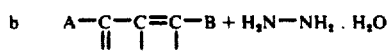

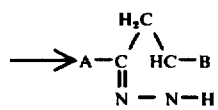

The symbols used in the above rection equations have the aforementioned meanings.

The reaction designated by Ia is performed in the presence of a solvent, such as an alcohol, for example ethanol. The reaction temperature is equal to the boiling point of the solvent used. The reaction Ib is also carried out in a solvent, such as ethanol, at an elevated temperature. The reaction IIa is performed in the presence of a solvent, such as methanol, at room temperature. The reaction conditions are made alkaline by the addition of a base, such as caustic soda. The reaction IIb also is carried out in the presence of a solvent, such as ethanol. The reaction temperature is equal to the boiling point of the solvent used.

The invention will be described more fully with reference to the following Examples.

1. Production of 1-(3,4-dichlorophenylcarbamoyl)-3-phenyl-$\Delta^2$-pyrazoline a. Production of β-dimethylaminopropiophenone hydrochloride of the formula

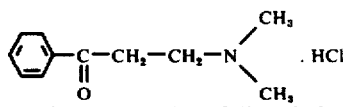

120 g of acetophenone, 105 g of dimethylamine hydrochloride and 39.6 g of paraformaldehyde were placed, together with 2 ml of concentrated hydrochloric acid and 160 ml of ethanol, in a round-bottomed flask or a 1 liter. After the resulting solution had been boiled for two hours it was filtered and diluted with 800 ml of acetone. The solution was allowed to stand for 16 hours at 0° C, after which the crystals formed were drawn off, washed with 50 ml of acetone and dried. The yield was 145 g of β-dimethylamino-propiophenone hydrochloride having a melting point of 155° C.

b. Production of 3-phenyl- $\Delta^2$-pyrazoline of the formula

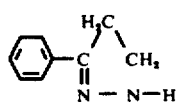

145 g of β-dimethylaminopropiophenone hydrochloride were added at a temperature of 50° C to a mixture of 105 ml of 100 % hydrazine hydrate, 69 ml of 40 % solution of caustic soda and 150 ml of methanol. The resulting mixture was boiled for 1 hour and, after standing overnight, diluted with 350 ml of water. The mixture was extracted thrice with ether, after which the ether layer was washed thrice with water. The extracts were dried over sodium sulfate and then distilled under nitrogen. Yield 51.5 g of 3-phenyl- $\Delta^2$-pyrazoline having a boiling point of 99°–100°/0.5 mm.

c. Production of 1-(3,4-dichlorophenylcarbamoyl)-3-phenyl- $\Delta^2$-pyrazoline of the formula

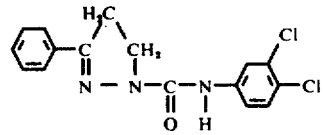

16.0 g of 3-phenyl- $\Delta^2$-pyrazoline were dissolved in 100 ml of ether. A solution of 20.4 g of 3,4-dichlorophenylisocyanate in 200 ml of ether was then added drop by drop with thorough stirring and cooling. After the addition was completed the reaction mixture was stirred for another 30 minutes. The precipitate formed was drawn off, washed with ether and dried. After recrystallization from acetonitrile 22 g of 1-(3,4-dichlorophenylcarbamoyl)3-phenyl- $\Delta^2$-pyrazoline having a melting point of 168°–169° C were obtained.

In a manner fully analogous to the aforedescribed one of the compounds 37–55 and 98–120 of the above list were prepared.

2. Production of 1-(4-chlorophenylcarbamoyl)-3-(4-chlorophenyl)-5-(4-chlorophenyl)- $\Delta^2$-pyrazoline Production of 4,4'-dichlorochalcone of the formula

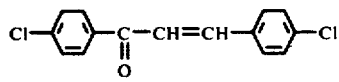

30.9 g of 4-chloroacetophenone and 28.1 g of 4-chlorobenzaldehyde were dissolved in 200 ml of methanol. 30 ml of 2N solution of caustic soda were added drop by drop with stirring and cooling to 20° C. After the reaction mixture had been stirred at 20° C for 2 hours, 20 ml of water were added and the resulting precipitate was drawn off. The precipitate was washed with water, then dried and washed again, this time with petroleumether (40°–60° C). The yield was 52.0 g of 4,4'-dichlorochalcone having a melting point of 151°–153° C.

b. Production of 3-(4-chlorophenyl)-5-(4-chlorophenyl)- $\Delta^2$-pyrazoline of the formula

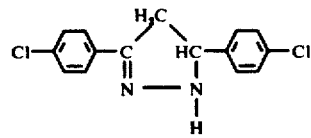

13.8 g of 4,4'-dichlorochalcone and 5 ml of 100% hydrazinehydrate were dissolved in 50 ml of ethanol and boiled for 1 hour. Then the alcohol was distilled off. The residue was cooled and treated with water. The resulting precipitate was drawn off, washed with water, taken up in 200 ml of ether and then dried over sodium sulfate under nitrogen.

c. Production of 1(4-chlorophenylcarbamoyl)-3-(4-chlorophenyl)-5-(4-chlorophenyl)- Δ²-pyrazoline of the formula

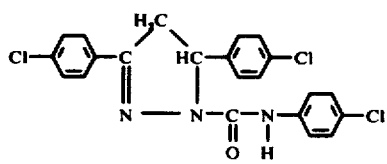

An ethereal solution of 7.6 g of 4-chlorophenylisocyanate was added drop by drop with stirring to the precipitate obtained by the process described in (b). 5 drops of triethylamine were added as a catalyst. The obtained white precipitate was dried. The yield was 18.4 g of 1-(4-chlorophenylcarbamoyl)-3-(4-chlorophenyl)-5-(4-chlorophenyl) Δ²-pyrazoline having a melting point of 222°–224° C.

In a manner analagous to the aforedescribed one the substances according to the invention denoted by the numbers 1 to 36 and 56 to 97 of the above list were prepared.

3. Wettable powders containing the active substances according to the invention were prepared by mixing 25 parts by weight of the active substance with 3 parts by weight of calciumligninsulphonate, 2 parts by weight of dibutylphthalenesulfonate and 70 parts by weight of kaolin.

4. Liquid concentrates of the active substances according to the invention were prepared by dissolving 10 parts by weight of the active substance in dimethylformamide, which may contain some cyclohexanone, after which 6 to 7 parts by weight of an emulsifier, such as mixture of nonylphenolpolyglycol ether and alkaline earth alkyl benzene sulfonate, were added to the solution.

5. The active substances according to the invention were dispersed in water in concentrations of 100, 30, 10, 3 and 1 mg of the active substance per liter of aqueous dispersion. Stems cut from potato plants were sprayed to dripping with an aqueous dispersion of the substance to be investigated and then placed in flasks filled with tap water. After the stems had dried, cylinders made of Perspex were slipped over them. Each stem was then infected with 5 larvae of *Leptinotarsa decemlineata* (Colorado beetle). The cylinders were covered with gauze and stored at a temperature of 24° C and a relative humidity of from 60% to 70%. After 5 days the per cent mortality of the larvae was determined. Each test was carried out in triplicate. The results of the test are shown in the following Table. The meanings of the symbole used in the Table are:

+ = from 90% to 100% mortality.
± = from 50% to 90% mortality.
− = less than 50% mortality.

TABLE

Biocidal activity against larvae of *Leptinotarsa decemlineata*

| Compound number according to the aforementioned list | Biocidal activity concentration expressed in mg of active substance per liter (p.p.m.) | | | | |
|---|---|---|---|---|---|
| | 100 | 30 | 10 | 3 | 1 |
| 1 | + | + | + | ± | − |
| 2 | + | + | + | + | ± |
| 3 | + | + | + | + | − |
| 4 | + | + | + | + | ± |
| 5 | + | + | + | ± | |
| 6 | + | + | + | + | ± |
| 7 | + | + | + | + | − |
| 8 | + | + | + | + | ± |
| 9 | + | + | + | + | − |
| 10 | + | + | + | + | ± |
| 11 | + | ± | − | | |
| 12 | + | + | + | + | |
| 13 | + | + | + | + | − |
| 14 | + | + | + | + | − |
| 15 | + | + | + | + | − |
| 16 | + | + | + | − | |
| 17 | + | + | + | ± | |
| 18 | + | + | + | − | |
| 19 | + | + | + | − | |
| 20 | + | ± | ± | ± | − |
| 21 | + | + | + | − | |
| 22 | + | + | + | − | |
| 23 | + | + | + | ± | − |
| 24 | + | + | + | ± | − |
| 25 | + | + | + | ± | − |
| 27 | + | + | + | ± | |
| 28 | + | + | + | − | |
| 29 | + | + | + | + | − |
| 30 | + | + | + | − | |
| 31 | + | + | + | + | − |
| 32 | + | + | + | − | |
| 33 | + | + | + | − | |
| 34 | + | + | + | + | |
| 35 | + | + | + | + | |
| 36 | + | + | + | | |
| 37 | + | + | + | + | − |
| 38 | + | + | + | + | − |
| 39 | + | + | + | + | − |
| 40 | + | + | + | + | − |
| 41 | + | + | + | + | |
| 42 | + | + | + | + | |
| 43 | + | + | + | ± | − |
| 44 | + | + | + | ± | − |
| 45 | + | + | + | − | |
| 46 | + | + | + | − | |

TABLE-continued

| Biocidal activity against larvae of *Leptinotarsa decemlineata* | | | | | |
|---|---|---|---|---|---|
| Compound | Biocidal activity | | | | |
| number according to the aforementioned list | concentration expressed in mg of active substance per liter (p.p.m.) | | | | |
|  | 100 | 30 | 10 | 3 | 1 |
| 47 | + | + | ± | − |  |
| 48 | + | + | + | − |  |
| 49 | + | + | + | − |  |
| 50 | + | + | ± | − |  |
| 51 | + | + | + | − |  |
| 52 | + | + | + | − |  |
| 53 | + | + | + | − |  |
| 54 | + | + | + |  |  |
| 55 | + | + | + |  |  |
| 56 | + | ± | − |  |  |
| 57 | + | ± | ± | − |  |
| 58 | + | ± | ± | − |  |
| 59 | + | + | − |  |  |
| 60 | + | + | ± |  |  |
| 61 | + | + | ± |  |  |
| 62 | + | − |  |  |  |
| 63 | + | + | − |  |  |
| 64 | + | − |  |  |  |
| 65 | + | + | − |  |  |
| 66 | + | + | ± |  |  |
| 67 | + | + | ± | ± | − |
| 68 | + | ± | − |  |  |
| 69 | + | + | − |  |  |
| 70 | ± | ± | ± | − |  |
| 71 | + | ± | ± | − |  |
| 72 | ± | ± | − |  |  |
| 73 | + | − |  |  |  |
| 74 | + | ± | ± | − |  |
| 75 | + | + | − |  |  |
| 76 | + | ± | − |  |  |
| 78 | + | + | ± | − |  |
| 79 | ± | − |  |  |  |
| 80 | + | + | − |  |  |
| 85 | ± |  |  |  |  |
| 86 | + | + | ± |  |  |
| 87 | + | + | ± |  |  |
| 88 | + | + | − |  |  |
| 89 | + | + | ± |  |  |
| 90 | + | + | ± | − |  |
| 91 | + | − |  |  |  |
| 92 | + | + | − |  |  |
| 93 | + | + |  |  |  |
| 94 | ± |  |  |  |  |
| 95 | + | + | ± |  |  |
| 96 | + | + | ± | − |  |
| 97 | + | + | ± | − |  |
| 98 | + | + | ± | − |  |
| 99 | + | + | − |  |  |
| 100 | + | − |  |  |  |
| 101 | + | − |  |  |  |
| 102 | + | + | − |  |  |
| 103 | + | + | ± | − |  |
| 104 | + | + | − |  |  |
| 105 | ± | − |  |  |  |
| 106 | + | + | ± | − |  |
| 107 | + | + | ± | − |  |
| 108 | + | + | − |  |  |
| 109 | + | + | − |  |  |
| 110 | + | + | − |  |  |
| 111 | + | + | − |  |  |
| 112 | + | + | − |  |  |
| 113 | + | ± |  |  |  |
| 114 | + | + | ± |  |  |
| 115 | + | + | ± |  |  |
| 116 | + | + | + |  |  |
| 117 | + | + | + |  |  |

What is claimed is:

1. A biocidal composition for controlling insects and mites, said composition containing, in addition to a solid or liquid inert carrier material, an insecticidally or miticidally effective amount of a pyrazoline of the formula

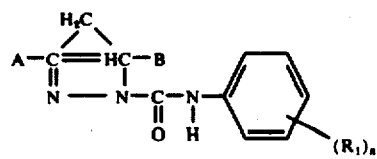

wherein

A is a moiety selected from the group consisting of phenyl and phenyl substituted by 1 or 2 substituents selected from the group consisting of halogen, cyano, alkyl of from 1 to 4 carbon atoms halogenated alkyl of from 1 to 4 carbon atoms, cyclohexyl, alkoxy of from 1 to 4 carbon atoms, alkylthio of from 1 to 4 carbon atoms and amino group substituted by 1 or 2 alkyls of 1 to 4 carbon atoms; each B is a moiety selected from the group consisting of hydrogen, phenyl and phenyl substituted by from 1 to 3 substituents selected from the group consisting of halogen, alkoxy of 1 to 4 carbon atoms, alkyl of 1 to 4 carbon atoms, optionally substituted with halogen thioalkyl of 1 to 4 carbon atoms, sulfonylalkyl of 1 to 4 carbon atoms, dioxy alkylene of 1 to 4 carbon atoms and amino substituted by 1 or 2 alkyl groups each alkyl having from 1 to 4 carbon atoms;

$R_1$ is a moiety selected from the group consisting of a halogen atom, alkoxy of 1 to 4 carbon atoms, alkyl of 1 to 4 carbon atoms, optionally substituted with halogen, thioalkyl of 1 to 4 carbon atoms, sulfonylalkyl of 1 to 4 carbon atoms, cyano, nitro and an amino group substituted by 1 or 2 alkyl groups, n is 1 or 2, with the proviso that when A represents a phenyl group containing two substituents, these substituents do not occupy the 2,6 positions of the phenyl group, and that $(R_1)_n$ must not be a 2,6-disubstitution.

2. The biocidal composition of claim 1 wherein the pyrazoline is of the formula

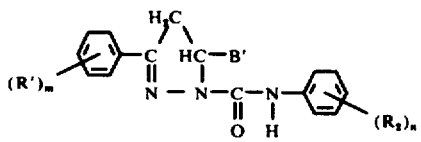

wherein

R' is a moiety selected from the group consisting of hydrogen, halogen, cyano, alkoxy of from 1 to 4 carbon atoms and alkyl of from 1 to 4 carbon atoms, B' is a moiety selected from the group consisting of hydrogen, phenyl, and phenyl substituted by from 1 to 3 substituents selected from the group consisting of halogen, alkoxy of from 1 to 4 carbon atoms and alkyl of from 1 to 4 carbon atoms, m is 1 or 2 and n is 1 or 2, with the proviso that $(R')_m$ and $(R_2)_n$ do not indicate substitution in both the 2 and 6 position 3. The biocidal composition of claim 1 wherein the pyrazoline is of the formula

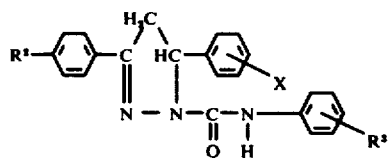

wherein $R^2$ is a moiety selected from the group consisting of hydrogen, halogen, cyano, alkyl, alkoxy and a thioalkyl group, each containing from 1 to 4 carbon atoms, cyclohexyl and amino group substituted by 1 or 2 alkyls, each alkyl containing from 1 to 4 carbon atoms, $R^3$ is a substituent in the para position selected from the group consisting of halogen, alkyl of from 1 to 4 carbon atoms optionally substituted with halogen, thioalkyl group of from 1 to 4 carbon atoms, sulfonylalkyl of from 1 to 4 carbon atoms, cyano and amino substituted by 1 or 2 alkyls, each alkyl containing from 1 to 4 carbon atoms or is a 3,4-dichloro substituent, and X is a substituent in the para position which is selected from the group consisting of hydrogen, halogen, alkyl of from 1 to 4 carbon atoms, cycloalkyl, alkoxy of from 1 to 4 carbon atoms and amino substituted by 1 or 2 alkyl groups each alkyl containing from 1 to 4 carbon atoms or a 2,4 or 3,4 disubstituent, the substituents being selected from the group consisting of halogen, lower alkyl and dioxyalkylene, or a 2,4,6-trihalogen group.

4. The biocidal composition of claim 1 wherein the pyrazoline is of the formula

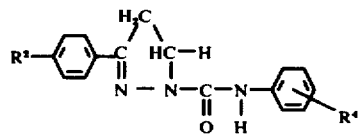

wherein $R^2$ has the meaning given in claim 1 and $R^4$ is a 3,4-dichloro group or a substituent in paraposition selected from the group consisting of halogen, alkyl of from 1 to 4 carbon atoms optionally substituted with halogen, a thioalkyl of from 1 to 4 carbon atoms, sulfonylalkyl of from 1 to 4 carbon atoms, cyano, nitro and amino group substituted by 1 or 2 alkyl groups each of from 1 to 4 carbon atoms.

5. The biocidal composition of claim 1 wherein the pyrazoline is of the formula

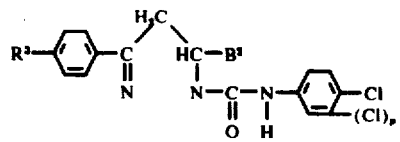

wherein $R^3$ is a moiety selected from the group consisting of hydrogen, halogen, cyano and methoxy, $B^2$ is a moiety selected from the group consisting of hydrogen, phenyl, 4-chlorophenyl, 4-methoxyphenyl and 2,4-dichlorophenyl and p = 0 or 1.

6. The biocidal composition as claimed in claim 1, wherein the pyrazoline is 1-(4-chlorophenylcarbamoyl)-3-(4-chlorophenyl)-5-(4-chlorophenyl)-$\Delta^2$-pyrazoline.

7. The biocidal composition as claimed in claim 1, wherein the pyrazoline is 1-(4-sulfonylmethylphenylcarbamoyl)-3-(4-chlorophenyl)-5-(4-chlorophenyl)-$\Delta^2$-pyrazoline.

8. The biocidal composition as claimed in claim 1, wherein the pyrazoline is 1-(4-sulfonylethylphenylcarbamoyl)-3-(4-chlorophenyl)-5-(4-chlorophenyl)-$\Delta^2$-pyrazoline.

9. The biocidal composition as claimed in claim 1, wherein the pyrazoline is 1-(4-chlorophenylcarbamoyl)-3-(4-chlorophenyl)-5-(4-isopropoxyphenyl)-$\Delta^2$-pyrazoline.

10. The biocidal composition as claimed in claim 1, wherein the pyrazoline is 1-(4-t.butylphenylcarbamoyl)-3-(4-chlorophenyl)-5-(4-chlorophenyl)-$\Delta^2$-pyrazoline.

11. The biocidal composition as claimed in claim 1, wherein the pyrazoline is 1-(4-n.propylphenylcarbamoyl)-3-(4-chlorophenyl)-5-(4-chlorophenyl)-$\Delta^2$-pyrazoline.

12. The biocidal composition as claimed in claim 1, wherein the pyrazoline is 1-(4-ethylphenylcarbamoyl)-3-(4-chlorophenyl)-5-(4-chlorophenyl)-$\Delta^2$-pyrazoline.

13. The biocidal composition as claimed in claim 1, wherein the pyrazoline is 1-(4-trifluoromethylphenylcarbamoyl)-3-(4-chlorophenyl)-5-(4-chlorophenyl)-$\Delta^2$-pyrazoline.

14. The biocidal composition as claimed in claim 1, wherein the pyrazoline is 1-(4-chlorophenylcarbamoyl)-3-(4-chlorophenyl)-5-(4-fluorophenyl)-$\Delta^2$-pyrazoline.

15. The biocidal composition as claimed in claim 1, wherein the pyrazoline is 1-(4-chlorophenylcabamoyl)-3-(4-chlorophenyl)-5-(4-ethylphenyl)-$\Delta^2$-pyrazoline.

16. The biocidal composition as claimed in claim 1, wherein the pyrazoline is 1-(4-chlorophenylcarbamoyl)-3-(4-chlorophenyl)-5-(4-t.butylphenyl)-$\Delta^2$-pyrazoline.

17. The biocidal composition as claimed in claim 1, wherein the pyrazoline is 1-(4-chlorophenylcarbamoyl)-3-(4-chlorophenyl)-5-(2-methyl-4-chlorophenyl)-$\Delta^2$-pyrazoline.

18. The biocidal composition as claimed in claim 1, wherein the pyrazoline is 1-(4-chlorophenylcarbamoyl)-3-(4-dimethylaminophenyl)-5-(4-chlorophenyl)-$\Delta^2$-pyrazoline.

19. The biocidal composition as claimed in claim 1, wherein the pyrazoline is 1-(4-chlorophenylcarbamoyl)-3-(4-chlorophenyl)-5-(2,4-dichlorophenyl)-$\Delta^2$-pyrazoline.

20. The biocidal composition as claimed in claim 1, wherein the pyrazoline is 1-(4-chlorophenylcarbamoyl)-3-phenyl-5-(4-methoxyphenyl)-$\Delta^2$-pyrazoline.

21. The biocidal composition as claimed in claim 1, wherein the pyrazoline is 1-(4-chlorophenylcarbamoyl)-3-phenyl-$\Delta^2$-pyrazoline.

22. The biocidal composition as claimed in claim 1, wherein the pyrazoline is 1-(chlorophenylcarbamoyl)-3-(4-chlorophenyl)-$\Delta^2$-pyrazoline.

23. The biocidal composition as claimed in claim 1, wherein the pyrazoline is 1-(4-chlorophenylcarbamoyl)-3-(4-fluorophenyl)-$\Delta^2$-pyrazoline.

24. The biocidal composition as claimed in claim 1, wherein the pyrazoline is 1-(4-chlorophenylcarbamoyl)-3-(4-bromophenyl-$\Delta^2$-pyrazoline.

25. The biocidal composition as claimed in claim 1, wherein the pyrazoline is 1-(4-iodophenylcarbamoyl)-3-(4-chlorophenyl)-$\Delta^2$-pyrazoline.

26. The biocidal composition as claimed in claim 1, wherein the pyrazoline is 1-(4-n.propylphenylcarbamoyl)-3-(4-chlorophenyl)-$\Delta^2$-pyrazoline.

27. The biocidal composition claimed in claim 1, wherein the pyrazoline is 1-(4-chlorophenylcarbamoyl)-3-(4-isopropoxyphenyl)-$\Delta^2$-pyrazoline.

28. The biocidal composition as claimed in claim 1, wherein the pyrazoline is 1-(4-ethylphenylcarbamoyl)-3-(4-chlorophenyl)-$\Delta^2$-pyrazoline.

29. The biocidal composition as claimed in claim 1, wherein the pyrazoline is 1-(4-ethylsulfonylphenylcarbamoyl)-3-(4-chlorophenyl)-$\Delta^2$-pyrazoline.

30. The biocidal composition as claimed in claim 1, wherein the pyrazoline is 1-(4-chlorophenylcarbamoyl)-3-(4-ethylphenyl)-$\Delta^2$-pyrazoline.

31. The biocidal composition as claimed in claim 1, wherein the pyrazoline is 1-(4-chlorophenylcarbamoyl)-3-(4-isopropylphenyl)-$\Delta^2$-pyrazoline.

32. The method of controlling insects and mites in agriculture and horticulture, wherein the infected areas are treated with a biocidal composition of claim 68 in a dosage which corresponds to from 0.5 to 5 kg of pyrazoline per hectare.

* * * * *